(12) United States Patent
Graham et al.

(10) Patent No.: US 7,179,253 B2
(45) Date of Patent: Feb. 20, 2007

(54) METHOD OF TATTOO REMOVAL

(75) Inventors: Paul D. Graham, Woodbury, MN (US);
Peter T. Elliott, Woodbury, MN (US);
Kevin G. Gallagher, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 82 days.

(21) Appl. No.: 10/799,960

(22) Filed: Mar. 12, 2004

(65) Prior Publication Data

US 2004/0181211 A1    Sep. 16, 2004

Related U.S. Application Data

(60) Provisional application No. 60/454,246, filed on Mar. 13, 2003.

(51) Int. Cl.
*A61B 18/04*    (2006.01)

(52) U.S. Cl. .............................. 606/9; 128/898; 607/89

(58) Field of Classification Search ................ 128/898; 606/9; 607/89; 514/293
See application file for complete search history.

(56) References Cited

U.S. PATENT DOCUMENTS

| | | |
|---|---|---|
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,376,501 A | 12/1994 | Mariën et al. |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,599,342 A * | 2/1997 | Hsia et al. ..................... 606/9 |

(Continued)

FOREIGN PATENT DOCUMENTS

EP    0 394 026    10/1990

(Continued)

OTHER PUBLICATIONS

Testerman, et al., "Cytokine Induction by the Immunomodulators Imiquimod and S-27609", *Journal of Leukocyte Biology*, vol. 58, pp. 365-372, Sep. 1995.

(Continued)

*Primary Examiner*—Henry M. Johnson, III
(74) *Attorney, Agent, or Firm*—Christopher D. Gram; Ted K. Ringsted; Robert W. Sprague

(57) ABSTRACT

A method for removing tattoos is disclosed. Generally, the method includes administering an IRM compound to the tattooed region. In some cases, the method also includes treating a tattooed area with a cell disrupter such as a laser beam.

15 Claims, 2 Drawing Sheets

U.S. PATENT DOCUMENTS

| | | | |
|---|---|---|---|
| 5,605,899 A | 2/1997 | Gerster et al. | |
| 5,693,811 A | 12/1997 | Lindstrom | |
| 5,741,908 A | 4/1998 | Gerster et al. | |
| 5,756,747 A | 5/1998 | Gerster | |
| 5,939,090 A | 8/1999 | Beaurline et al. | |
| 6,028,076 A | 2/2000 | Hirota et al. | |
| 6,039,969 A | 3/2000 | Tomai et al. | |
| 6,069,149 A | 5/2000 | Nanba et al. | |
| 6,083,505 A | 7/2000 | Miller et al. | |
| 6,110,929 A | 8/2000 | Gerster et al. | |
| 6,113,918 A | 9/2000 | Johnson et al. | |
| 6,194,388 B1 | 2/2001 | Krieg et al. | |
| 6,194,425 B1 | 2/2001 | Gerster et al. | |
| 6,197,020 B1* | 3/2001 | O'Donnell, Jr. | 606/9 |
| 6,200,592 B1 | 3/2001 | Tomai et al. | |
| 6,207,646 B1 | 3/2001 | Krieg et al. | |
| 6,239,116 B1 | 5/2001 | Krieg et al. | |
| 6,245,776 B1 | 6/2001 | Skwierczynski et al. | |
| 6,254,596 B1* | 7/2001 | Lawandy | 606/9 |
| 6,303,347 B1 | 10/2001 | Johnson et al. | |
| 6,323,200 B1 | 11/2001 | Gerster et al. | |
| 6,329,381 B1 | 12/2001 | Kurimoto et al. | |
| 6,331,539 B1 | 12/2001 | Crooks et al. | |
| 6,339,068 B1 | 1/2002 | Krieg et al. | |
| 6,376,501 B1 | 4/2002 | Isobe et al. | |
| 6,376,669 B1 | 4/2002 | Rice et al. | |
| 6,387,938 B1 | 5/2002 | Mizuguchi et al. | |
| 6,406,705 B1 | 6/2002 | Davis et al. | |
| 6,426,334 B1 | 7/2002 | Agrawal et al. | |
| 6,440,992 B1 | 8/2002 | Gerster et al. | |
| 6,451,810 B1 | 9/2002 | Coleman et al. | |
| 6,476,000 B1 | 11/2002 | Agrawal | |
| 6,514,985 B1 | 2/2003 | Gerster et al. | |
| 6,518,265 B1 | 2/2003 | Kato et al. | |
| 6,518,280 B2 | 2/2003 | Gerster et al. | |
| 6,525,028 B1 | 2/2003 | Johnson et al. | |
| 6,525,064 B1 | 2/2003 | Dellaria et al. | |
| 6,541,485 B1 | 4/2003 | Crooks et al. | |
| 6,545,016 B1 | 4/2003 | Dellaria et al. | |
| 6,545,017 B1 | 4/2003 | Dellaria et al. | |
| 6,558,951 B1 | 5/2003 | Tomai et al. | |
| 6,573,273 B1 | 6/2003 | Crooks et al. | |
| 6,649,172 B2 | 11/2003 | Johnson | |
| 6,656,938 B2 | 12/2003 | Crooks et al. | |
| 6,660,735 B2 | 12/2003 | Crooks et al. | |
| 6,660,747 B2 | 12/2003 | Crooks et al. | |
| 6,664,260 B2 | 12/2003 | Charles et al. | |
| 6,664,264 B2 | 12/2003 | Dellaria et al. | |
| 6,664,265 B2 | 12/2003 | Crooks et al. | |
| 6,667,312 B2 | 12/2003 | Bonk et al. | |
| 6,670,372 B2 | 12/2003 | Charles et al. | |
| 6,677,347 B2 | 1/2004 | Crooks et al. | |
| 6,677,348 B2 | 1/2004 | Heppner et al. | |
| 6,677,349 B1 | 1/2004 | Griesgraber | |
| 6,683,088 B2 | 1/2004 | Crooks et al. | |
| 6,749,602 B2* | 6/2004 | Sierra et al. | 606/9 |
| 2002/0016332 A1 | 2/2002 | Slade | |
| 2002/0055517 A1 | 5/2002 | Smith | |
| 2002/0058674 A1 | 5/2002 | Hedenstrom et al. | |
| 2002/0110840 A1 | 8/2002 | Tomai et al. | |
| 2003/0022302 A1 | 1/2003 | Lewis et al. | |
| 2003/0133913 A1 | 7/2003 | Tomai et al. | |
| 2003/0139364 A1 | 7/2003 | Krieg et al. | |
| 2003/0144283 A1 | 7/2003 | Coleman et al. | |
| 2003/0199461 A1 | 10/2003 | Averett et al. | |
| 2004/0010007 A1 | 1/2004 | Dellaria et al. | |
| 2004/0014779 A1 | 1/2004 | Gorden et al. | |
| 2004/0023870 A1 | 2/2004 | Dedera et al. | |

FOREIGN PATENT DOCUMENTS

| | | |
|---|---|---|
| EP | 1 104 764 A1 | 6/2001 |
| JP | 11-80156 | 3/1999 |
| JP | 11-222432 | 8/1999 |
| JP | 2000-247884 | 9/2000 |
| WO | WO 00/47719 A2 | 8/2000 |
| WO | WO 00/75304 A1 | 12/2000 |
| WO | WO 00/76505 A1 | 12/2000 |
| WO | WO 00/76518 A1 | 12/2000 |
| WO | WO 01/74343 A2 | 10/2001 |
| WO | WO 02/36592 A1 | 5/2002 |
| WO | WO 02/46188 A2 | 6/2002 |
| WO | WO 02/46189 A2 | 6/2002 |
| WO | WO 02/46190 A2 | 6/2002 |
| WO | WO 02/46191 A2 | 6/2002 |
| WO | WO 02/46192 A2 | 6/2002 |
| WO | WO 02/46193 A2 | 6/2002 |
| WO | WO 02/46194 A2 | 6/2002 |
| WO | WO 02/46749 A2 | 6/2002 |
| WO | WO 02/085905 A1 | 10/2002 |
| WO | WO 02/102377 A1 | 12/2002 |
| WO | WO 03/020889 A2 | 3/2003 |
| WO | WO 03/043572 A2 | 5/2003 |
| WO | WO 03/045391 A1 | 6/2003 |
| WO | WO 03/089602 | 10/2003 |
| WO | WO 03/103584 A2 | 12/2003 |

OTHER PUBLICATIONS

Chollet, et al, "Development of a Topically Active Imiquimod Formulation", *Pharmaceutical Development and Technology*, 4(1), pp. 35-43 (1999).

Brassard et al.; "Interferon-α as an immunotherapeutic protein"; Journal of Leukocyte Biology; vol. 71; Apr. 2002; pp. 565-581.

Izumi et al.; "1H-imidazo[4,5-c]quinoline Derivatives as Novel Potent TNF-α Suppressors: Synthesis and Structure-Activity Relationship of 1-, 2-and 4-Substituted 1H-imidazo[4,5-c]quinolines or 1H-imidazo[4,5-c]pyridines"; *Bioorganic and Medicinal Chemistry*, vol. 11, pp. 2541-2550 (2003).

Hornung et al., "Quantitative Expression of Toll-Like Receptor 1-10 mRNA in Cellular Subsets of Human Peripheral Blood Mononuclear Cells and Sensitivity to CpG Oligodeoxynucleotides" *The Journal of Immunology*, 2002, 168; pp. 4531-4537.

Hemmi et al., "Small anti-viral compounds activate immune cells via the TLR7 MyD88-dependent Signaling pathway", *Nature Immunology*, vol. 3, No. 2; Feb. 2002; pp. 196-200.

Medzhitov, "Toll-Like Receptors and Innate Immunity", *Nature Reviews Immunology*, vol. 1; Nov. 2001, pp. 135-145.

Jurk et al. "Human TLR7 and TLR8 independently confer responsiveness to the antiviral compound R-848", *Nature Immunology*, Jun. 2002, vol. 3, No. 6; p. 1.

Akira et al., "Toll-like receptors: critical proteins linking innate and acquired immunity", *Nature Immunology*, Aug. 2001, vol. 2, No. 8; pp. 675-680.

Heil et al.; "Synthetic immunostimulatory compounds activate immune cells via TLR7 and TLR8"; 33th Annual Meeting of the Deutsche Gessellshaft für Immunologie, Marburg 2002 - Abstract C.6.

Solis et al.; "Experimental Nonsurgical Tattoo Removal in a Guinea Pig Model with Topical Imiquimod and Tretinoin"; American Society for Dermatologic Surgery, Inc.; 28: Jan. 1, 2002; pp. 83-87.

Ferguson et al.; "The Q-switched neodymium: YAG laser and tattoos: a microscopic analysis of laser-tattoo interactions"; British Journal of Dermatology; 1997; 117: 405-410.

Baumier et al.; "Q-Switch Laser and Tattoo Pigments: First Results of the Chemical and Photophysical Analysis of 41 Compounds"; Lasers in Surgery and Medicine; 26: 13-21 (2000).

Patipa et al.; "Light and Electron Microscopic Findings with Permanent Eyeliner"; Ophthalmology; Oct. 1986; vol. 93; No. 10; pp. 1361-1365.

Anderson et al.; "Selective Photothermolysis: Precise Microsurgery by Selective Absorption of Pulsed Radiation"; Science, vol. 220; Apr. 1983; pp. 524-527.

Rosenberg et al.; "Lasers in Aesthetic Surgery"; Clinics in Plastic Surgery; vol. 23, No. 1; Jan. 1996; pp. 29-48.

Wheeland; "Clinical Uses of Lasers in Dermatology"; Lasers in Surgery and Medicine; 16:2-23 (1995).

Zelickson et al.; "Clinical, Histologic, and Ultrastructural Evaluation of Tattoos Treated With Three Laser Systems"; Lasers in Surgery and Medicine; 15:364-372 (1994).

Aghassi et al; "Complications of Aesthetic Laser Surgery"; Annals of Plastic Surgery; vol. 43; No. 5; Nov. 1999; pp. 560-569.

Adrian et al.; "Laser Tattoo Removal"; Aesthetic Laser Surgery—Clinics in Plastic Surgery; vol. 27; No. 2; Apr. 2000; pp. 181-192.

Jimenez et al.; "Multiple Color Changes Following Laser Therapy of Cosmetic Tattoos"; Dermatol Surg.; 28:2:Feb. 2002; pp. 177-179.

Armstrong et al.; "Motivation for Tattoo Removal"; Arch Dermatol; vol. 132, Apr. 1996; pp. 412-416.

Brown et al.; "Youth and Tattoos: What School Health Personnel Should Know."; Journal of School Health; 70; 9; 355; Nov. 2000; pp. 26-29.

Anderson; "Regarding Tattoos—Is That Sunlight, or an Oncoming Train at the End of the Tunnel?"; Arch Dermatol; vol. 137, Feb. 2001; pp. 210-212.

Taylor et al.; "Light and Electron Microscopic Analysis of Tattoos Treated by Q-Switched Ruby Laser"; The Journal of Investigative Dermatology; vol. 97 No. 1, July. 1991; pp. 131-136.

Newspaper article entitled "Tattoo Undo"; Variety Section Star Tribune (Mpls-St. Paul); Apr. 8, 2000; 4 pgs.

Akira S. et al., "Recognition of pathogen-associated molecular patterns by TLR family", *Immunology Letters*, 2003, vol. 85, pp. 85-95.

Ozinsky A. et al. "The repertoire for pattern recognition of pathogens by the innate immune system is defined by cooperation between Toll-like receptors", *Proc. Nat. Acad. Sci.*, Dec. 2000, vol. 97, No. 25, pp. 13766-13771.

Gorden et al., "Synthetic TLR Agonists Reveal Functional Differences between Human TLR7 and TLR8", *The Journal of Immunology*, 2005, vol. 174, pp. 1259-1268.

Sauder et al., "Randomized, Single-Blind, Placebo-Controlled Study of Topical Application of the Immune Response Modulator Resiquimod in Healthy Adults", *Antimicrobial Agents and Chemotherapy*, Dec. 2003, vol. 47, No. 12, pp. 3846-3852.

* cited by examiner

METHOD OF TATTOO REMOVAL

CROSS-REFERENCE TO RELATED APPLICATION

This application claims priority to U.S. Provisional Patent Application No. 60/454,246, filed Mar. 13, 2003.

BACKGROUND OF THE INVENTION

Modern tattoo inks generally include organic pigment particles ranging in size from about 200 nanometers to about 5 micrometers. They are typically inserted into the papillary and superficial dermis by a rapidly reciprocating needle. Following injection, the tattoo ink pigment particles reside in the interstitial space between dermal cells for about 24–72 hours, although in some cases pigment particles may reside in interstitial spaces for up to two weeks. Eventually, dermal cells (typically fibroblasts or macrophages) engulf the pigment particles. Once the pigment particles have been engulfed, they usually reside within the cell cytoplasm. The dermal cells typically have low motility, which accounts for the relative permanence of most tattoo images.

Recently, tattoos have become increasingly popular. For instance, the tattoo industry ranked sixth in a 1996 study that estimated the growth rates of various industries (Brown et al., *J. School Health* 70(9):355 (2000)). The practice of permanent tattooing has become so widespread that it is now estimated that as many as 30 million people in the Western world have at least one tattoo (Baumier et al., *Lasers in Surgery and Medicine* 26:13–21 (2000)).

Some who choose to be tattooed may at some later date regret the decision. The spirit, motivation, and/or circumstances that compelled one to obtain a tattoo can fade. In some cases, a tattoo that was appropriate or desirable at one station of life may be less appropriate or less desirable at a later date. Depending upon the nature and extent of the tattoo image, an unwanted tattoo may be a nuisance, a source of embarrassment, or even a source of social stigmatization. Perhaps as a direct result of the increased popularity of tattoos, interest in tattoo removal also is increasing. Market estimates suggest that in the year 2000 as many as 410,000 people underwent a tattoo removal procedure. As the recently tattooed population ages, it is expected that the number of those seeking removal of a tattoo will increase.

Current treatment options for tattoo removal include a variety of lasers, dermabrasion, salabrasion, surgical excision, and cryotherapy. Although some treatments may be effective, they may be expensive, time consuming, and painful. In some cases, such treatments also may result in cosmetically undesirable scarring.

One of the more effective tattoo removal treatments is a laser surgical technique in which the tattooed region is irradiated with a high-energy, pulsating laser beam. The tattoo ink pigments absorb a portion of the laser radiation. As a consequence, the pigment particles become sufficiently hot that they decompose into smaller fragments (Ferguson, J. E. et al., *British Journal of Dermatology* 137: 405–410 (1997)). In the process, the cellular integrity of the surrounding dermal cells may be destroyed. A single laser treatment results in some fading of the tattoo because the human immune system is able to remove some of the pigment fragments (Wheeland, *Lasers in Surgery and Medicine* 16:2–23 (1995); Zelickson et al., *Lasers in Surgery and Medicine* 15:364–372 (1994)); however, most pigment fragments become re-engulfed by still intact dermal cells and so remain visible (Ferguson et al., *British Journal of Dermatology* 137:405–410 (1997)). In nearly all cases, patients are not satisfied with the results of the first laser treatment and they usually return for additional treatments.

Irradiating the tattooed region with enough energy to fragment the tattoo ink pigments can cause a painful burn to form on the skin. Consequently, laser treatments are sometimes spaced at least one month apart in order to afford the skin time to heal. Often, as many as nine such treatments may be required to sufficiently fade the tattoo, resulting in substantial pain and financial cost.

The laser treatment procedure may be ineffective for removing certain colors and may, instead of removing an image, transform some colors such as, for example, transforming a red lipstick tattoo to a black shade that can be very difficult to remove by laser surgical treatment (Jimenez et al., *Dermatolog. Surg.* 28:177–179 (2002)).

Immune response modifiers ("IRMs") are compounds that possess potent immunomodulating activity such as, for example, antiviral and/or antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,541,485; 6,545,016; 6,545,017; 6,558,951; 6,573,273; 6,656,938;.6,660,735; 6,660,747; 6,664,260; 6,664,264; 6,664,265; 6,667,312; 6,670,372; 6,677,347; 6,677,348; 6,677,349; 6,683,088; European Patent 0 394 026; U.S. Pat. Publication Nos. 2002/0016332; 2002/0055517; 2002/0110840; 2003/0133913; 2003/0199538; and 2004/0014779; and International Patent Publication Nos. WO 01/74343; WO 02/46749 WO 02/102377; WO 03/020889; WO 03/043572; WO 03/045391; and WO 03/103584.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/085905), and certain 3-β-D-ribofuranosylthiazolo[4,5-d] pyrimidine derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303, 347; 6,525,028; and 6,649,172.

One IRM compound has been shown to effective for removing freshly applied tattoos (Solis et al., *Dermatol Surg.* 28:83–87 (2002)). Solis et al. tattooed a group of guinea pigs with a commonly used set of tattoo inks. Topical treatment of the tattooed area with 5% imiquimod (1-(2-methylpropyl)-1H-imidazo[4,5-c]quinolin-4-amine) cream, marketed as ALDARA (3M Pharmaceuticals, St. Paul, Minn.), was initiated within six hours of the tattoo application and continued for seven days. At the conclusion of the treatment period, no pigment of any color was visible in the tattooed regions. Thus, an IRM compound applied to a recently tattooed area has been shown to remove tattoo ink pigments while they are still in the free extracellular (i.e., interstitial) space of the dermis. However, a need remains for methods of removing mature tattoos—i.e., tattoo images that are days, not merely hours, old.

SUMMARY OF THE INVENTION

It has been found that certain IRM compounds can be useful in methods for removing tattoos.

Accordingly, the present invention provides a method of tattoo removal that includes treating a tattooed region with a cell disrupter and administering to the tattooed region an effective amount of an IRM compound.

In another aspect, the present invention provides a method of removal of a mature tattoo that includes administering to a tattooed region an effective amount of an IRM compound.

In certain embodiments, the IRM compound is administered as a composition. In certain embodiments, the IRM compound is administered via a topical application vehicle such as a cream, a gel, a foam, a spray, an ointment, a lotion, a solution, a suspension, an emulsion, a microemulsion, a dispersion, a paste, a powder, or an oil. In other embodiments the IRM compound is administered via a transdermal patch.

In certain embodiments, treatment with a cell disrupter takes place before the administration of an IRM compound.

In certain embodiments, treatment with a cell disrupter takes place after the administration of an IRM compound.

In certain embodiments, treatment with a cell disrupter takes place coincident with the administration of an IRM compound.

In some embodiments, the IRM compound is an agonist of at least one Toll-like receptor (TLR) such as, for example, TLR4, TLR7, TLR8, or TLR9.

In certain embodiments the cell disrupter may be a laser. For example, in some embodiments, the laser may be a Q-switched Nd:YAG laser (532 nanometers), a Q-switched Nd:YAG laser (1064 nanometers), a Q-switched ruby laser (694 nanometers), a Q-switched alexandrite laser (755 nanometers), an argon laser, a carbon dioxide laser, an ER:YAG laser, or a combination. In some embodiments, the laser may contact the tattooed region under conditions sufficient to disrupt dermal cells and disrupt pigment particles. In certain alternative embodiments, the laser contacts the tattooed region under conditions sufficient to disrupt dermal cells but inadequate to disrupt all or many of the pigment particles.

Various other features and advantages of the present invention should become readily apparent with reference to the following detailed description, examples, claims and appended figures. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1A:
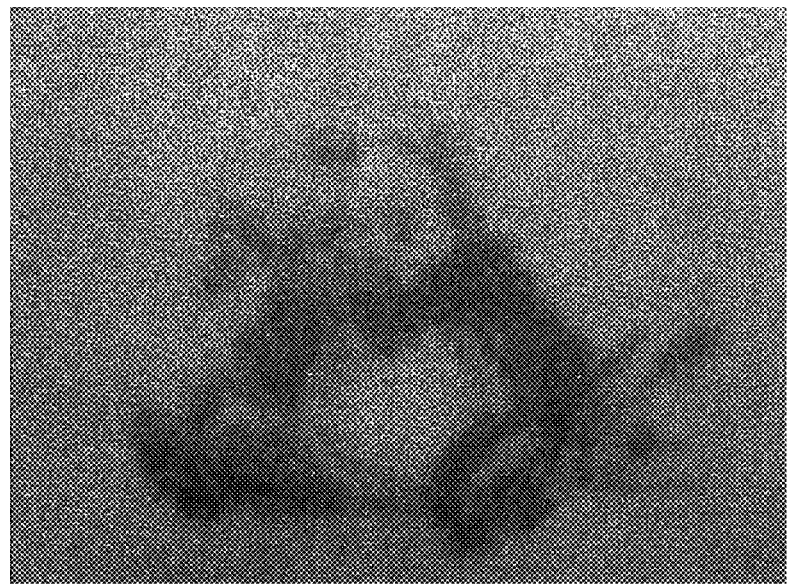
FIGS. 1A–D are photographs from one subject receiving treatment of one tattoo with laser therapy and 1× daily administration IRM (FIGS. 1A and 1B) compared to a second tattoo treated with laser therapy and 1× daily administration of placebo (FIGS. 1C and 1D).

The present invention provides methods for removing a tattoo. Generally, the methods include administering an IRM compound to a tattooed region. In some embodiments of the invention, the tattooed region is treated with a cell disruptor and an effective amount of an IRM compound. The IRM compound may be administered before, after, or at the same time as, the tattooed region is treated with a cell disruptor. In an alternative embodiment, the IRM is administered to a tattooed region containing a mature tattoo, without treatment with a cell disruptor.

When the method includes use of a cell disruptor, the tattooed region may be treated with the cell disruptor in an amount sufficient to both disrupt dermal cells and to fragment ink pigment particles. Alternatively, the tattooed region may be treated with a cell disruptor in an amount sufficient to disrupt dermal cells but insufficient to fragment ink pigment particles.

As used herein, "tattooed region" and variations thereof refer generally to any area of skin that includes tattoo ink. A tattooed region may include area that does not include tattoo ink such as, for example, area between tattoo images, area between portions of a tattoo image, and area beyond the margin of the image. A tattooed region may include any portion of a tattoo image or any portion of tattoo images on an individual having multiple tattoos.

A cell disruptor suitable for practicing the invention may be any known means of treating dermal cells so that the cellular integrity of dermal cells in the tattooed region is destroyed. A cell disruptor may or may not also cause ink pigment particles contained within the dermal cells of a tattooed region to fragment. A cell disruptor may include mechanical, chemical, and/or thermal means of disrupting dermal cells. A cell disruptor can include, for example, liquid nitrogen, a chemical peel, an abrasive agent, and/or electromagnetic radiation.

Cell disruptors that have been used for the removal of tattoos have included the topical application of mild acids, salabrasion, cryosurgery, dermabrasion, and thermal cautery methods such as, for example electrocoagulation and infrared coagulation. See, for example, Adrain et al., *Clinics in Plastic Surgery,* 27, 181 (2000) and Goldstein et al., *J. Dermatol. Surg. Oncol.* 5:901 (1979). A preferred cell disruptor for removing tattoos is a high-energy, pulsating beam of electromagnetic radiation. See, for example, Rosenberg and Gregory *Clinics in Plastic Surgery,* 1996; 23:2948; Anderson and Parrish, *Science,* 1983; 220:524–527; Wheeland, *Lasers Surg. Med.,* 1995; 16:2–23; Zelickson et al., *Lasers Surg. Med.,* 1994; 15:364–372; Aghassi et al.,

*Annals of Plastic Surgery,* 1999; 43:560–569; Adrain and Griffin, *Aesthetic Laser Surgery,* 2000; 27:181–192; and Taylor et al., *The Journal of Investigative Dermatology,* 1991; 97:131–136.

Suitable electromagnetic radiation may be substantially monochromatic or it may be polychromatic. In some cases, the wavelength of the electromagnetic radiation may range from about 200 nanometers to about 1300 nanometers, although some embodiments of the invention may be practiced using electromagnetic radiation having a wavelength outside this range. In some cases, the electromagnetic radiation is delivered to the tattoo region as a series of short pulses. In some cases, the length of pulse is less than one microsecond, in other cases less than 100 nanoseconds, and in still other cases less than one nanosecond.

The electromagnetic radiation may be generated in any conventional manner capable of generating an amount of energy sufficient to disrupt dermal cells. In some cases, the electromagnetic radiation is generated by a laser.

Lasers used for tattoo removal include, but are not limited to, argon lasers, carbon dioxide lasers, Er:YAG lasers, Q-switched ruby lasers, Q-switched alexandrite lasers, and Q-switched Nd:YAG lasers (Adrain et al., *Clinics in Plastic Surgery,* 27, 181 (2000)). Lasers that are commonly used in tattoo removal include the Q-switched Nd:YAG laser (532 nm and/or 1064 nm); Q-switched ruby laser (694 nm); and the Q-switched alexandrite laser (755 nm) (see, for example, Solis et al., *Dermatol. Surg.* 28:83087 (2002); and Rosenberg and Gregory, *Clinics in Plastic Surgery* 23(1):29–48 (1996)). In one particular embodiment, a Q-switched Nd:YAG laser (532 nm) may be used as a cell disruptor. In another embodiment, a Q-switched Nd:YAG laser (1064 nm) may be used as a cell disruptor. In another embodiment, a Q-switched alexandrite (755 nm) laser may be used as a cell disrupter. In other embodiments, a combination of lasers may be used.

A study by Taylor et al. (*The Journal of Investigative Dermatology* 97: 131–136 (1991)) shows that a single laser surgical tattoo removal procedure results in the disruption of all of the dermal cells that are proximate to the tattoo ink pigment particles and, consequently, the pigment particles are released into the free extracellular space of the dermis. While a fraction of these extracellular tattoo ink pigment particles will be removed by the immune system, many again undergo phagocytosis and are fixed into the dermis, where they remain unless and/or until they are subjected to additional laser treatment.

The method of the present invention may be performed to remove a mature tattoo. A mature tattoo is defined herein as a tattoo in which most of the tattoo ink pigment particles have been engulfed by, and reside in the cytoplasm of, dermal cells such as, for example, macrophages and fibroblasts.

Alternatively, the method of the present invention may be performed to remove freshly applied or immature tattoos. A freshly applied or immature tattoo may be less than one week old, for example, 24–72 hours old. In a freshly applied tattoo or an immature tattoo, a majority of the tattoo ink pigment particles remain free in the interstitial space between dermal cells. Histological analysis of freshly applied tattoos (Patipa et al., *Ophthalmology,* 93(10):1361–1365 (1986)) shows that the tattoo ink pigment particles remain in the free extracellular space of the dermal cells for several days (about 24–72 hours) before the pigment particles are engulfed by macrophages and/or fibroblast cells.

IRM compounds suitable for use in the invention may include the purine derivatives, imidazoquinoline amide derivatives, benzimidazole derivatives, adenine derivatives, aminoalkyl glucosaminide phosphates, and oligonucleotide sequences described above. In addition, in some embodiments of the present invention, the IRM compound may include a 2-aminopyridine fused to a five membered nitrogen-containing heterocyclic ring, or a 4-aminopyrimidine fused to a five membered nitrogen-containing heterocyclic ring.

In some embodiments, the IRM compound may be, for example, an imidazoquinoline amine including but not limited to amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines. Various combinations of IRMs can be used if desired.

In one particular embodiment, the IRM compound is an imidazoquinoline amine such as, for example, 1-(2-methylpropyl)-1H-imidazo[4,5-c]quinolin-4-amine or 4-amino-α,α-dimethyl-2-ethoxymethyl-1H-imidazo[4,5-c]quinolin-1-ethanol.

In an alternative embodiment, the IRM compound is an imidazonaphthyridine amine such as, for example, 2-methyl-1-(2-methylpropyl)-1H-imidazo[4,5-c][1,5]naphthyridin-4-amine or 1-(2-methylpropyl)-1H-imidazo[4,5-c][1,5]naphthyridin-4-amine.

In another alternative embodiment, the IRM compound is a sulfonamide substituted imidazoquinoline amine such as, for example, N-[4-(4-amino-2-ethyl-1H-imidazo[4,5-c]quinolin-1-yl)butyl]methanesulfonamide.

In another alternative embodiment, the IRM compound is an amide substituted imidazoquinoline amine such as, for example, N-{2-[4-amino-2-(ethoxymethyl)-1H-imidazo[4, 5-c]quinolin-1-yl]-1,1-dimethylethyl}cyclohexanecarboxamide.

In another alternative embodiment, the IRM compound is a thioether substituted imidazoquinoline amine such as, for example, 2-butyl-1-[2-(propylsulfonyl)ethyl]-1H-imidazo [4,5-c]quinolin-4-amine.

In yet another alternative embodiment, the IRM compound is an imidazopyridine amine such as, for example, N-{2-[4-amino-2-(ethoxymethyl)-6,7-dimethyl-1H-imidazo [4,5-c]pyridin-1-yl]ethyl}benzamide.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

Certain IRMs can function as Toll-like receptor (TLR) agonists, i.e., their immunomodulating influence is exerted through a TLR-mediated cellular pathway. For example, some small molecule IRMs have been identified as agonists of one or more members of the TLR receptor family, TLR2, TLR4, TLR6, TLR7, and TLR8; certain AGPs have been identified as agonists of TLR4; and, some CpGs has been identified as an agonist of TLR9. In many cases, activating a TLR-mediated pathway results in gene transcription, cytokine or co-stimulatory marker expression regardless of the particular TLR that is activated.

In certain embodiments of the present invention, the IRM compound is an agonist of at least one TLR. In particular embodiments, the IRM compound can be an agonist of TLR4, TLR7, TLR8, and/or TLR9. In one particular embodiment, the IRM compound is an agonist of TLR8 or an agonist of both TLR7 and TLR8. In an alternative embodiment, the IRM compound is an agonist of TLR4. The IRM may induce the production of one or more cytokines, including but not limited to, Type I interferons, TNF-α, IL-10, and IL-12. See, for example, Gibson et al., *Cell Immunol.* 218(1–2):74–86 (2002). The IRM may effect the maturation, activation, and/or migration of cells of the myeloid lineage such as, for example, macrophages, dendritic cells, and Langerhans cells.

The IRM compound may be administered to a tattooed region before, after, and/or at the same time as, a treatment of the tattooed region with a cell disruptor. In some embodiments, the IRM compound is administered within about 20 days of a treatment with the cell disruptor—i.e., at least one administration of IRM compound sometime from about 20 days before treatment with the cell disruptor to about 20 days after treatment with the cell disruptor—although the invention may be practiced by administering the IRM compound to the tattooed region outside of this period. In some embodiments, the IRM compound is administered within about 10 days of a treatment with a cell disruptor such as, for example, within about 5 days of a treatment with a cell disruptor or within about 3 days of a treatment with a cell disruptor. In one particular embodiment, the IRM compound is administered at least once within about 24 hours of a treatment with a cell disrupter. In another particular embodiment, the IRM compound is administered at least once within about 12 hours of a treatment with a cell disrupter. Alternatively, in certain embodiments, the IRM compound may be administered to a tattooed region without treatment with a cell disrupter.

In one embodiment, an IRM may be administered to a tattooed region containing a mature tattoo—i.e., a tattoo that is at least 7 days old. For example, a mature tattoo may be more than one week old (for example, at least 2 weeks old, at least 3 weeks old, at least 4 weeks old, at least 5 weeks old or at least 6 weeks old), one or more months old (for example, at least two months old, at least 3 months old, at least 4 months old, at least 5 months old, at least 6 months old, at least 7 months old, at least 8 months old, at least 9 months old, at least 10 months old, at least 11 months old, at least 12 months old, at least 16 months old, or at least 18 months old) or one or more years old (for example, at least 1 year old, at least 2 years old, at least 3 years old, at least 4 years old, at least 5 years old, at least 10 years old, or at least 25 years old). In one particular embodiment, the IRM compound is administered to a tattooed region that includes a tattoo that is at least six months old.

In some embodiments, the IRM compound may be administered to a tattooed region containing a freshly applied or immature tattoo—i.e., a tattoo that is less than 7 days old. For example, a freshly applied tattoo may be less than about 72 hours old such as, for example, less than about 48 hours old or less than about 24 hours old. In certain embodiments, an immature tattoo may be from about 1 day old to about 7 days old, for example, about 1 day old, about 2 days old, about 3 days old, about 4 days old, about 5 days old, about 6 days old, and about 7 days old.

The compound may be provided in any formulation suitable for administration to a subject. Suitable types of formulations are described, for example, in U.S. Pat. No. 5,736,553; U.S. Pat. No. 5,238,944; U.S. Pat. No. 5,939,090; U.S. Pat. No. 6,365,166; U.S. Pat. No. 6,245,776; U.S. Pat. No. 6,486,186; European Patent No. EP 0 394 026; and U.S. Pat. Publication No. 2003/0199538. The compound may be provided in any suitable form including but not limited to a solution, a suspension, an emulsion, or any form of mixture. The compound may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a foam, a solution, a suspension, a dispersion, an emulsion, a microemulsion, a paste, a powder, a solid stick (e.g., wax- or petroleum-based sticks), a wipe, an oil, a lotion, and the like. In one particular embodiment, the IRM compound is provided in a cream formulation suitable for topical administration.

A formulation suitable for practicing the invention may include one or more additional active ingredients such as, for example, another IRM compound, an antibiotic, a pain reliever, a skin penetration enhancer, or a topical anesthetic. In some embodiments, the IRM compound may be incorporated into, for example, a sunscreen, a skin lotion, a skin moisturizer, or cosmetic. Alternatively, the IRM compound may be incorporated into any vehicle suitable for intradermal or transdermal delivery.

The composition of a suitable formulation may depend at least in part on many factors known in the art including but not limited to the physical and chemical nature of the IRM compound; the nature of the carrier; the dosing regimen; the state of the subject's immune system (e.g., suppressed, compromised, stimulated); the method of administering the IRM compound; the age of the tattoo; the type of pigments contained within the tattoo; the skill and/or experience of the person who applied the tattoo; the effectiveness of the cell disrupter, if provided; the overall size of the tattoo; and the desired result (i.e., reduction or complete removal). Accordingly it is not practical to set forth generally a single formulation suitable for removing tattoos for all possible applications. Those of ordinary skill in the art, however, can readily determine a suitable formulation with due consideration of such factors.

A suitable formulation may contain, for example, about 0.001%, about 0.002%, about 0.005%, about 0.01%, about 0.015%, about 0.02%, about 0.025%, about 0.05%, about 0.1%, about 0.25%, about 0.5%, about 0.75%, about 1%, about 2.5%, about 5%, about 7.5%, about 10%, about 25%, or about 50% active IRM compound. In one particular embodiment, the composition includes about 5% IRM compound.

The dosing regimen may depend at least in part on many factors known in the art including but not limited to the physical and chemical nature of the IRM compound; the nature of the carrier; the amount of IRM being administered; the state of the subject's immune system (e.g., suppressed, compromised, stimulated); the method of administering the IRM compound; the age of the tattoo; the type of pigments contained within the tattoo; the skill and/or experience of the person who applied the tattoo; the effectiveness of the cell disrupter, if provided; the overall size of the tattoo; and the desired result (i.e., reduction or complete removal). Accordingly it is not practical to set forth generally the dosing regimen effective for removing tattoos for all possible applications. Those of ordinary skill in the art, however, can readily determine the appropriate dosing regimen with due consideration of such factors.

In some embodiments of the invention, the IRM compound may be administered, for example, from a single dose to multiple doses administered multiple times per day. In certain embodiments, the IRM compound may be administered from about once per week to about once per day. In one particular embodiment, the IRM compound is administered once per day. In an alternative embodiment, the IRM compound is administered once every other day.

After an IRM compound is administered to a tattooed region, the tattooed area may or may not be covered with a bandage. For example, if a laser treatment has been administered, post procedure care may be as described, for example, by Rosenberg and Gregory (*Clinics in Plastic Surgery* 23(1):29–48 (1996)) or as otherwise directed by a medical professional.

As used herein, "effective amount" of an IRM compound is an amount that promotes clearance of a tattoo image (i.e., causes the image to fade and/or speeds disappearance, etc.). In certain embodiments, an effective amount of an IRM compound promotes full clearance (i.e., complete removal, disappearance) of the treated tattoo image. In other embodiments, an effective amount of IRM compound need only promote fading of the treated tattoo image.

The particular amount of IRM compound that constitutes an effective amount may depend, at least in part, on one or more factors. Such factors include, but are not limited to, the particular IRM compound being administered, the state of the subject's immune system (e.g., suppressed, compromised, stimulated); the route of administering the IRM; the age of the tattoo; the type of pigments contained within the tattoo; the skill and/or experience of the person who applied the tattoo; the effectiveness of the cell disrupter; the overall size of the tattoo; and the desired result (i.e., reduction or complete removal). Accordingly, it is not practical to set forth generally the amount that constitutes an effective amount of an IRM compound. Those of ordinary skill in the art, however, can readily determine the appropriate amount with due consideration of such factors.

In some embodiments, the methods of the present invention include administering sufficient IRM compound to provide a dose of, for example, from about 100 ng/kg to about 50 mg/kg to the subject, although in some embodiments the method may be performed by administering IRM compound in a dose outside this range. In some of these embodiments, the method includes administering sufficient IRM compound to provide a dose of from about 10 µg/kg to about 5 mg/kg to the subject, for example, a dose of from about 100 µg/kg to about 1 mg/kg.

The methods of the present invention may be performed on any suitable subject. Suitable subjects include, but are not limited to, animals such as but not limited to humans, non-human primates, rodents, dogs, cats, horses, pigs, sheep, goats, or cows.

EXAMPLES

Twenty volunteers seeking tattoo removal treatment were enrolled in a study. All subjects sought removal of two tattoos, each tattoo being at least six months old, within ten years of age of the other tattoo, and of similar pigment color spectrum, intensity, and sharpness to the other. The treatment area for any given tattoo ranged from 1 in.$^2$ to 2 in.$^2$ (2.5 cm$^2$ to 5 cm$^2$).

Laser treatment was performed every four to six weeks for a maximum of six laser treatments or until a tattoo was completely cleared. A Q-switched Nd:YAG laser set at 1064 nm was used to treat blue and black pigments. A frequency doubled Nd:YAG laser set at 532 nm was used to treat red pigments. A Q-switched alexandrite 755 nm laser was used to treat aqua and green pigments.

In combination with the laser treatment, one of each subject's tattoos was randomly selected to receive treatment with 5% imiquimod cream (ALDARA, 3M Pharmaceuticals, St. Paul, Minn.) by topical administration. The other tattoo received topical application of a placebo cream that contained no biologically active agent. Each dose of the imiquimod and placebo creams was individually packaged. Topical treatments (imiquimod and placebo) were performed 1× per day starting one week before the first laser treatment session. All subjects completed a follow-up visit two weeks after the first laser treatment session for examination of the treated tattoo regions.

Digital photographs (Nikon 5000, NikonUSA, Inc., Melville, N.Y.) of each tattoo region were taken at the initial visit, at every laser treatment session prior to the laser treatment, and four weeks after the last laser treatment. Photographs were taken under identical light settings and electronically stored.

Figure 1B:
Figure 1C:
Figure 1D:
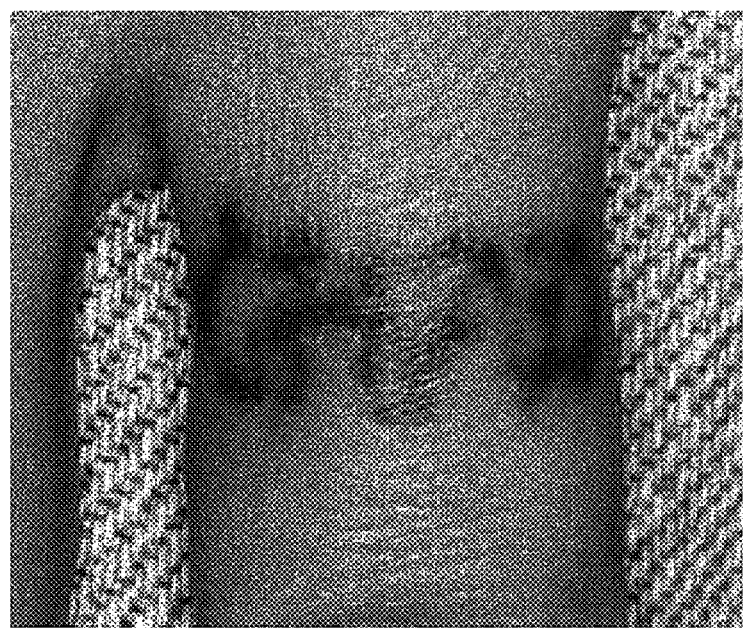

FIGS. 1A–D are digital photographs taken from one subject at the initial visit (FIGS. 1A and 1C) and at one month after three laser treatments (FIGS. 1B and 1D)—after half of the maximum number of laser treatments. The tattoo shown in FIGS. 1A and 1B received 1× daily treatment with 5% imiquimod. The tattoo shown in FIGS. 1C and 1D received 1× daily treatment with placebo cream.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method for removing a mature tattoo comprising:
   treating at least a portion of a tattooed region comprising a mature tattoo with a cell disrupter; and
   administering to at least a portion of the tattooed region an amount of an IRM compound effective for fading the tattoo.

2. The method of claim 1 wherein the IRM compound is administered as a composition comprising an IRM compound.

3. The method of claim 1 wherein the treatment with a cell disrupter takes place before the administration of an IRM compound.

4. The method of claim 1 wherein the treatment with a cell disrupter takes place after the administration of an IRM compound.

5. The method of claim 1 wherein the treatment with a cell disrupter takes place coincident with the administration of an IRM compound.

6. The method of claim 1 wherein the IRM compound is administered via a topical application vehicle.

7. The method of claim 6 wherein the topical application vehicle comprises a cream, a gel, a foam, a spray, an ointment, a lotion, a solution, a suspension, a dispersion, an emulsion, a microemulsion, a paste, a powder, or an oil.

8. The method of claim 1 wherein the IRM compound is administered via a transdermal patch.

9. The method of claim 1 wherein the IRM compound is an agonist of at least one TLR.

10. The method of claim 9 wherein the IRM compound is an agonist of one or more of TLR7, TLR8, and TLR9.

11. The method of claim 1 wherein the IRM compound is an imidazoquinoline amine; a tetrahydroimidazoquinoline amine; an imidazopyridine amine; a 1,2-bridged imidazoquinoline amine; a 6,7-fused cycloalkylimidazopyridine amine; an imidazonaphthyridine amine; a tetrahydronaphthyridine amine; an oxazoloquinoline amine; a thiazoloquinoline amine; an oxazolopyridine amine; a thiazolopyridine amine; an oxazolonaphthyridine amine; a thiazolonaphthyridine amine; or a 1H-imidazo dimer fused to a pyridine amine, a quinoline amine, a tetrahydroquinoline amine, a naphthyridine amine, or a tetrahydronaphthyridine amine.

12. The method of claim 1 wherein the cell disrupter is a laser.

13. The method of claim 12 wherein the laser is selected from the group consisting of a Q-switched Nd:YAG laser (532 nanometers), a Q-switched Nd:YAG laser (1064 nanometers), a Q-switched ruby laser (694 nanometers), a Q-switched alexandrite laser (755 nanometers), an argon laser, a carbon dioxide laser, an Er:YAG laser, and combinations thereof.

14. The method of claim 12 wherein the laser contacts the tattooed region under conditions sufficient to disrupt dermal cells and disrupt pigment particles.

15. The method of claim 12 wherein the laser contacts the tattooed region under conditions sufficient to disrupt dermal cells but inadequate to disrupt all or many of the pigment particles.

* * * * *